US009550065B2

(12) United States Patent
Kornet et al.

(10) Patent No.: US 9,550,065 B2
(45) Date of Patent: Jan. 24, 2017

(54) SELECTION OF SPINAL CORD STIMULATION ELECTRODES FOR USE IN CARDIAC THERAPY

(71) Applicant: Medtronic, Inc., Minneapolis, MN (US)

(72) Inventors: Lilian Kornet, Maastricht (NL); Tim D. J. Jongen, Schinnen (NL); Raphael A. Schneider, Maastricht (NL); Pascalle H. C. M. Reiters, Gronsveld (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/180,826

(22) Filed: Jun. 13, 2016

(65) Prior Publication Data

US 2016/0296758 A1     Oct. 13, 2016

Related U.S. Application Data

(63) Continuation of application No. 13/192,822, filed on Jul. 28, 2011, now Pat. No. 9,364,670.

(51) Int. Cl.
*A61N 1/36* (2006.01)
*A61N 1/05* (2006.01)

(52) U.S. Cl.
CPC ......... *A61N 1/36185* (2013.01); *A61N 1/0551* (2013.01); *A61N 1/36057* (2013.01); *A61N 1/36114* (2013.01); *A61N 1/36139* (2013.01)

(58) Field of Classification Search
CPC .................... A61N 1/36114; A61N 1/36117
See application file for complete search history.

(56) References Cited

U.S. PATENT DOCUMENTS

| | | |
|---|---|---|
| 4,044,774 A | 8/1977 | Corbin et al. |
| 4,549,556 A | 10/1985 | Tarjan et al. |
| 5,255,691 A | 10/1993 | Otten |
| 5,292,336 A | 3/1994 | Spence, Jr. et al. |
| 5,331,966 A | 7/1994 | Bennett et al. |
| 5,360,441 A | 11/1994 | Otten |
| 5,417,719 A | 5/1995 | Hull et al. |
| 6,134,470 A | 10/2000 | Hartlaub |
| 7,146,223 B1 | 12/2006 | King |
| 7,155,278 B2 | 12/2006 | King et al. |
| 7,218,964 B2 | 5/2007 | Hill et al. |
| 9,364,670 B2 | 6/2016 | Kornet et al. |
| 2006/0195159 A1 | 8/2006 | Bradley et al. |
| 2008/0004674 A1 | 1/2008 | King et al. |
| 2010/0016919 A1 | 1/2010 | Hill et al. |

OTHER PUBLICATIONS

Armoundas et al., "A novel pacing method to suppress repolarization alternans in vivo: Implications for arrhythmia prevention," *Heart Rhythm*, Apr. 2013; 10(4):564-572.

(Continued)

*Primary Examiner* — Amanda Patton
(74) *Attorney, Agent, or Firm* — Carol F. Barry

(57) ABSTRACT

Methods, systems, and/or devices for selecting spinal cord stimulation (SCS) electrode array configurations to provide effective cardiac therapy. Physiological parameters related to the heart may be monitored and analyzed during the delivery of SCS using various SCS electrode array configurations to determine an effect SCS electrode array configuration.

16 Claims, 5 Drawing Sheets

(56) References Cited

OTHER PUBLICATIONS

Bloomfield et al., "Microvolt T-wave alternans and the risk of death or sustained ventricular arrhythmias in patients with left ventricular dysfunction," *J. Am. Coll. Cardiol.*, Jan. 17, 2006; 47(2):456-463. Available online Dec. 15, 2005.

Chow et al., "Usefulness of microvolt T-wave alternans on predicting outcome in patients with ischemic cardiomyopathy with and without defibrillators," *American Journal of Cardiology*, Mar. 2007; 100(4):598-604. Available online Jun. 28, 2007.

DeJongste, "Spinal cord stimulation for ischemic heart disease," *Neurol. Res.*, Apr. 2000; 22(3):293-298.

Felber Dietrich et al., "Heart rate variability in an ageing population and its association with lifestyle and cardiovascular risk factors: results of the Sapaldia study," Europace, Jul. 2006; 8(7):521-529.

Ferrero et al., "Spinal cord stimulation affects T-wave alternans in patients with ischaemic cardiomyopathy: a pilot study," *Europace*, Apr. 2008; 10:506-508. Available online Mar. 12, 2008.

Foreman et al., "Modulation of intrinsic cardiac neurons by spinal cord stimulation: implications for its therapeutic use in angina pectoris," *Cardiovascular Research*, 2000; 47:367-375.

"Heart Rate Turbulence: What is HRT?," [Online]. Technische Universität München. Last updated Mar. 27, 2007 [retrieved on Jul. 27, 2011]. Retrieved from the internet: <URL:http://www.h-r-t.com/hrt/en/index.html>; 1 pg.

Holsheimer et al., "Effects of electrode configuration and geometry on fiber preference in spinal cord stimulation," *Proceedings of the 18$^{th}$ Annual International Conference of the IEEE*, Oct. 31-Nov. 3, 1996; 1:343-344.

Myles et al., "Is microvolt T-wave alternans the answer to risk stratification in heart failure?" *Circulation*, Dec. 18, 2007; 116(25):2984-2991.

Schmidt et al., "Heart-rate turbulence after ventricular premature beats as a predictor of mortality after acute myocardial infarction," *The Lancet*, Apr. 24, 2999; 353:1390-1396.

Wilson et al., "Mechanisms of arrythmogenic cardiac alternans," *Europace*, 2007; 9:vi77-vi82.

SELECTION OF SPINAL CORD STIMULATION ELECTRODES FOR USE IN CARDIAC THERAPY

This application is a continuation of U.S. patent application Ser. No. 13/192,822, filed on Jul. 28, 2011, which is incorporated herein by reference in its entirety.

The disclosure herein relates to selection of spinal cord stimulation electrodes for use in cardiac therapy, and further to systems and devices for performing and implementing such methods.

Spinal cord stimulation (SCS) may be used to restore autonomic balance by inhibiting sympathetic stimulation of the heart, which may positively affect angina, heart failure, and the occurrence of ventricular arrhythmias. Accumulating evidence demonstrates that SCS may be a safe anti-anginal treatment that may not hide myocardial infarction symptoms. Further, it has been shown that SCS may modify the capacity of intrinsic cardiac neurons to generate activity. SCS may also act to suppress the excitatory effects that the local myocardial ischemia exerts on such neurons.

SCS may also improve contractility, to further improve the pressure-volume relationship within the heart, and to reduce sympathetic activity of the cardiac tissue to reduce the likelihood of ventricular arrhythmias. The electrical stimulation delivered by SCS may produce effects similar to those induced by prescription beta-blocker drugs, which has been shown to vasodilate peripheral arterioles and increase blood flow to the limbs. SCS may further cause the production of neuropeptides such as CGRP, NO, and VIP that are known vasodilators, which may assist in redirection of blood flow from regions of high flow to regions of low flow and improve the efficiency of the heart. In ischemic dilated cardiomyopathy patients, SCS may suppress or reduce sub-endocardial ischemia, and hence be cardio-protective. SCS may further result in improvements to the operational efficiency and function of cardiac tissue even in the presence of reduced blood supply.

A SCS system generally includes a plurality of electrodes located on at least one electrode lead. The electrode lead is implanted in a patient such that the electrodes are located along the spinal cord (e.g., the dura of the spinal cord). Electrical stimulation (e.g., electrical pulses) may then be delivered through the electrodes to the nerve fibers within the spinal cord for therapeutic effect.

Electrode arrays used in SCS systems often employ between 4 and 16 electrodes. Each of the electrodes may be selectively configured in an active state (e.g., functional to deliver electrical stimulation) or an inactive state (e.g., nonfunctional to deliver electrical stimulation), and further, may be configured in a negative polarity or in a positive polarity when in an active state.

SUMMARY

Exemplary methods, systems, and/or devices described herein may analyze one or more physiological parameters related to a patient's heart while delivering spinal cord stimulation (SCS) therapy using a plurality of different electrode array configurations to determine the effectiveness of each of the plurality of electrode array configurations. For example, heart rate turbulence and/or T-wave alternans (TWA) may be analyzed for SCS delivered from each different electrode array configuration. If heart rate turbulence and/or T-wave alternans changes (e.g., such that autonomic function is improved) in response to the delivery of SCS using an electrode array configuration, it may indicate that the electrode array configuration is effective.

One exemplary system (e.g., including an implantable medical device) disclosed herein for use in delivering spinal cord stimulation for providing cardiac therapy (e.g., for use in the treatment of heart failure) may include stimulation apparatus configured to provide spinal cord stimulation to a patient, sensing apparatus configured to monitor one or more parameters related to the patient's heart, and a control module coupled to the sensing apparatus and to the stimulation apparatus.

The stimulation apparatus may include a plurality of electrodes located along the patient's spinal cord. The plurality of electrodes may be coupled to one or more spinal leads. Each electrode of the plurality of electrodes may be locatable at a different location along the patient's spinal cord and each electrode of the plurality of electrodes may be configurable in one of an active state and an inactive state and is further configurable in one of a negative polarity and a positive polarity when in the active state.

The control module may be configured to define a plurality of electrode array configurations using the plurality of electrodes for use in delivery of spinal cord stimulation. Each electrode array configuration of the plurality of electrode array configurations may be configured differently than the other electrode array configurations of the plurality of electrode array configurations. The control module may be further configured to use each different electrode array configuration separately from the other electrode array configurations to deliver spinal cord stimulation for cardiac therapy and monitor (e.g., using the sensing apparatus) one or more physiological parameters related to the patient's heart during the delivery of spinal cord stimulation from each different electrode array configuration of the plurality of electrode array configurations. The control module may be further configured to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy (e.g., analyze the one or more physiological for changes that may correlate to or indicate an improvement in heart functionality).

In another exemplary system (e.g., including an implantable medical device) disclosed herein for use in delivering spinal cord stimulation for providing cardiac therapy (e.g., for use in the treatment of heart failure), the control module may be configured to define at least a first electrode array configuration and a second electrode array configuration, each for use in delivery of spinal cord stimulation. The first electrode array configuration may be configured differently than the second electrode array configuration. The control module may be further configured to use each of the first electrode array configuration and the second electrode array configuration separately from each other to deliver spinal cord stimulation for cardiac therapy, monitor (e.g., using the sensing apparatus) one or more physiological parameters related to the patient's heart during the delivery of spinal cord stimulation from each of the first and the second electrode array configurations, and analyze the one or more physiological parameters monitored during the delivery of spinal cord stimulation from each of the first and the second electrode array configurations to determine the more effective electrode array configuration of the first electrode array configuration and the second electrode array configuration for use in delivering spinal cord stimulation for cardiac therapy (e.g., analyze the one or more physiological for changes that may correlate to or indicate an improvement in heart functionality).

In one exemplary method of delivering spinal cord stimulation described herein for providing cardiac therapy (e.g., for use in the treatment of heart failure), the exemplary method may include providing a plurality of electrodes located along a patient's spinal cord. Each electrode of the plurality of electrodes may be located at a different location along the patient's spinal cord, and each electrode of the plurality of electrodes may be configurable in one of an active state and an inactive state and is further configurable in one of a negative polarity and a positive polarity when in the active state. The exemplary method may further include defining a plurality of electrode array configurations using the plurality of electrodes for use in delivery of spinal cord stimulation. Each electrode array configuration of the plurality of electrode array configurations may be configured differently than the other electrode array configurations of the plurality of electrode array configurations. The exemplary method may further include using each different electrode array configuration separately from the other electrode array configurations to deliver spinal cord stimulation for cardiac therapy and monitoring one or more physiological parameters related to the patient's heart during the delivery of spinal cord stimulation from each different electrode array configuration of the plurality of electrode array configurations. The exemplary method may further include analyzing the one or more physiological parameters monitored during the delivery of spinal cord stimulation from each different electrode array configuration to select an effective electrode array configuration of the plurality of electrode array configurations in delivering spinal cord stimulation for cardiac therapy (e.g., analyze the one or more physiological for changes that may correlate to or indicate an improvement in heart functionality).

In another exemplary method of delivering spinal cord stimulation disclosed herein for use providing cardiac therapy (e.g., for use in the treatment of heart failure) may include defining at least a first electrode array configuration and a second electrode array configuration each for use in delivery of spinal cord stimulation. The first electrode array configuration may be configured differently than the second electrode array configuration. The exemplary method may include using each of the first electrode array configuration and the second electrode array configuration separately from each other to deliver spinal cord stimulation for cardiac therapy, monitoring one or more physiological parameters related to the patient's heart during the delivery of spinal cord stimulation from each of the first and the second electrode array configurations, and analyzing the one or more physiological parameters monitored during the delivery of spinal cord stimulation from each of the first and the second electrode array configurations to determine the more effective electrode array configuration of the first electrode array configuration and the second electrode array configuration for delivering spinal cord stimulation for cardiac therapy (e.g., analyze the one or more physiological for changes that may correlate to or indicate an improvement in heart functionality).

In one or more exemplary methods and/or control modules of exemplary systems, analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy may include one or more of the following: analyzing T-wave alternans during the delivery of spinal cord stimulation from each different electrode array configuration and determining the effectiveness of each different electrode array configuration based on a decrease in T-wave alternans; analyzing heart rate turbulence during the delivery of spinal cord stimulation from each different electrode array configuration and determining the effectiveness of each different electrode array configuration based on a change in heart rate turbulence; analyzing heart rate during the delivery of spinal cord stimulation from each different electrode array configuration and determining the effectiveness of each different electrode array configuration based on a decrease in heart rate; analyzing heart rate variability during the delivery of spinal cord stimulation from each different electrode array configuration and determining the effectiveness of each different electrode array configuration based on a change in heart rate variability; analyzing repolarization variability during the delivery of spinal cord stimulation from each different electrode array configuration and determining the effectiveness of each different electrode array configuration based on a decrease in repolarization variability; analyzing baroreflex sensitivity during the delivery of spinal cord stimulation from each different electrode array configuration and determining the effectiveness of each different electrode array configuration based on an increase in baroreflex sensitivity; analyzing changes in one or more segments of monitored electrocardiogram signals during the delivery of spinal cord stimulation from each different electrode array configuration and determining the effectiveness of each different electrode array configuration based on the changes in one or more segments of the electrocardiogram signals; and analyzing electrical activity of the patient's vagus nerve proximate the patient's heart during the delivery of spinal cord stimulation from each different electrode array configuration and determining the effectiveness of each different electrode array configuration based on an increase in the electrical activity of the patient's vagus nerve.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
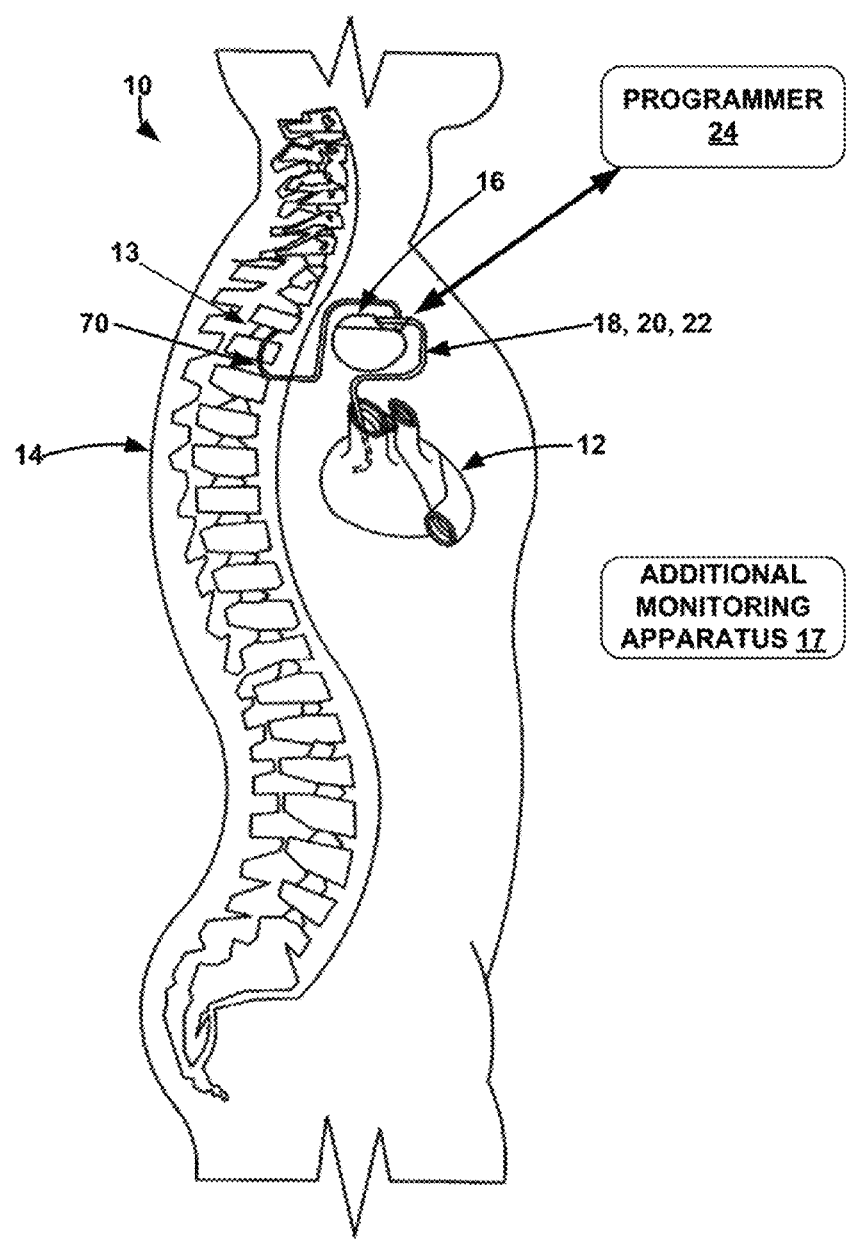
FIG. 1 is a diagram of an exemplary system including an exemplary implantable medical device (IMD).
Figure 2:
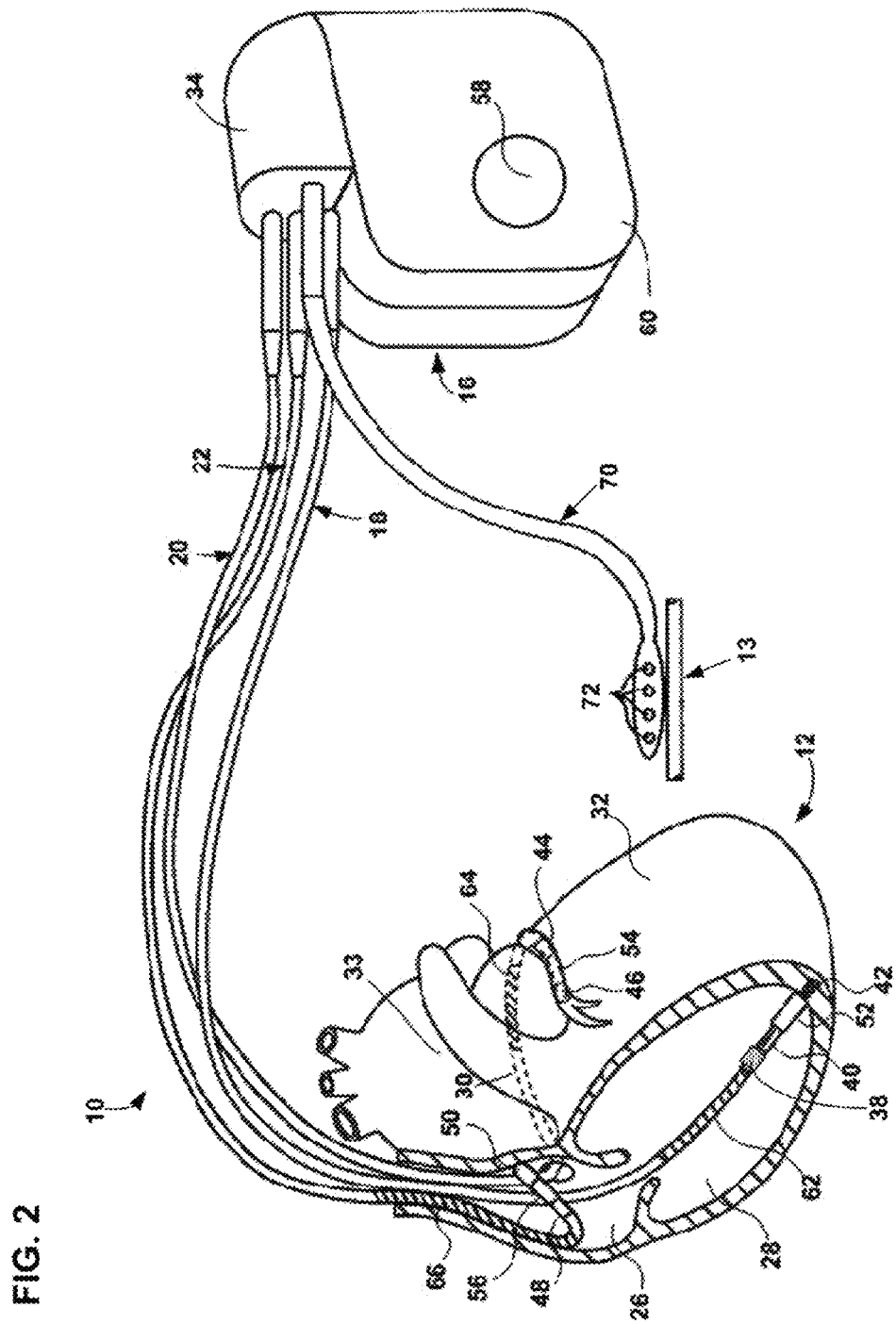
FIG. 2 is a diagram of the IMD of FIG. 1.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described with reference to FIGS. 1-5. It will be apparent to one skilled in the art that elements or processes from one embodiment may be used in combination with elements or processes of the other embodiments, and that the possible embodiments of such methods, devices, and systems using combinations of features set forth herein is not limited to the specific embodiments shown in the figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

FIG. 1 is a conceptual diagram illustrating an exemplary therapy system 10 that may be used in the delivery of cardiac therapy (e.g., SCS, pacing therapy, etc.) (e.g., for use in the treatment of heart failure) and/or in the monitoring of one or more physiological parameters of a patient 14. The patient 14 may, but not necessarily, be a human. The exemplary therapy system 10, as shown, may include an implantable medical device 16 (IMD) that is implanted pectorally and includes a spinal cord lead 70 implanted such that its electrodes are located adjacent the spinal column, for example, in the epidural or intrathecal space, between C6 and T4 (e.g., in the vicinity of T1). In at least one embodiment, the distal end of the lead 70, which carries electrodes 72, may be positioned between C6 and T2, in order to obtain a paresthesic stimulation of the sternal region. The IMD 16 further includes leads 18, 20, 22, which are implanted in the heart, as illustrated in more detail in FIG. 2.

The exemplary therapy system 10 may include an implantable medical device 16 (IMD), which may be coupled to leads 18, 20, 22, 70 and a programmer 24. The IMD 16 may be, e.g., an implantable spinal cord stimulator, pacemaker, cardioverter, and/or defibrillator, that provides electrical signals (e.g., stimulation pulses) to the spinal cord 13 of a patient 14 via electrodes coupled to the lead 70 and/or to the heart 12 of a patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 2, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing pulses to the heart 12 based on the electrical signals sensed within the heart 12. The configurations of the electrodes used by the IMD 16 for sensing and pacing may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses.

The SCS lead 70 may be implanted in the patient 14 such that the electrodes 72 are located along the spinal cord. In at least one embodiment, the SCS lead 70 may be of the type described in U.S. Pat. No. 4,549,556 issued to Tarjan et al. or in commonly assigned U.S. Pat. No. 5,255,691 issued to Otten, U.S. Pat. No. 4,044,774 issued to Corbin et al. or U.S. Pat. No. 5,360,441 issued to Otten, which are all incorporated herein by reference in their entireties, or may correspond to commercially available spinal cord stimulation leads such as the Medtronic® Model 3487A or 3888 leads.

More specifically, the SCS lead 70 may include a plurality of spaced apart electrodes 72 that are adapted to be placed adjacent the spinal cord 13, for example in the intrathecal space or in the epidural space or adjacent the roots of nerves branching off of the spinal cord. Although the SCS lead 70 shown in FIG. 2 includes four electrodes 72, a SCS lead 70 may, e.g., include 2 electrodes to 36 electrodes. Further, although as depicted the system 10 only includes a single SCS lead 70, the system 10 may include two or more SCS leads, each providing a plurality of electrodes configured to be located proximate a patient's spinal cord to deliver SCS.

In some examples, the programmer 24 may be a handheld computing device or a computer workstation, which a user, such as a physician, technician, other clinician, and/or patient 14 may use to communicate with the IMD 16. For example, the user may interact with the programmer 24 to retrieve and/or transmit physiological and/or diagnostic information (e.g., one or more physiological parameters, etc.) from the IMD 16.

The IMD 16 and the programmer 24 may communicate via wireless communication using any techniques known in the art. Examples of communication techniques may include, e.g., low frequency or radiofrequency (RF) telemetry, but other techniques are also contemplated.

The leads 18, 20, 22, 70 may be electrically coupled to a therapy delivery module (e.g., the lead 70 may be coupled to a SCS pulse generator), a sensing module, and/or any other modules of the IMD 16 via a connector block 34. In some examples, the proximal ends of the leads 18, 20, 22, 70 may include electrical contacts that electrically couple to respective electrical contacts within the connector block 34 of the IMD 16. In addition, in some examples, the leads 18, 20, 22, 70 may be mechanically coupled to the connector block 34 with the aid of set screws, connection pins, or another suitable mechanical coupling mechanism.

Each of the leads 18, 20, 22, 70 may include an elongated insulative lead body, which, e.g., may carry a number of concentric coiled conductors, or straight conductors, separated from one another by insulative material. In the illustrated example, a pressure sensor 38 and bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22. As shown, the pressure sensor 38 is disposed in the right ventricle 28 of the patient's heart 12. The pressure sensor 38 may respond to an absolute pressure inside the right ventricle 28, and may be, e.g., a capacitive and/or piezoelectric pressure sensor. In other examples, the pressure sensor 38 may be positioned within other regions of the heart 12 (e.g., the left ventricle) and may monitor pressure within one or more of the other regions of the heart 12, or may be positioned elsewhere within or proximate to the cardiovascular system of the patient 14 to monitor cardiovascular pressure associated with mechanical contraction of the heart.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the coiled conductors within the lead body of its associated lead 18, 20, 22, and thereby coupled to a respective one of the electrical contacts on the proximal end of the leads 18, 20, 22.

The electrodes 40, 42, 44, 46, 48, 50 may further be used to sense electrical signals attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12 (e.g., for use in CRT). In some examples, the IMD 16 includes one or more housing electrodes, such as housing electrode 58, which may be formed integrally with an outer surface of a housing 60 (e.g., hermetically-sealed housing) of the IMD 16 or otherwise coupled to the housing 60.

The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66, and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes.

The pressure sensor 38 may be coupled to one or more conductors within the lead 18. As shown, the pressure sensor 38 is located more distally on the lead 18 than the elongated electrode 62. In other examples, the pressure sensor 38 may be positioned more proximally than the elongated electrode 62, rather than distal to the electrode 62. Further, the pressure sensor 38 may be coupled to another one of the leads 20, 22 in other examples, or to a lead other than the leads 18, 20, 22 carrying stimulation and sense electrodes. In addition, for example, the pressure sensor 38 may be self-contained device that is implanted within the heart 12, such as within the septum separating the right ventricle 28 from the left ventricle 32, or the septum separating the right atrium 26 from the left atrium 33. In such an example, the pressure sensor 38 may wirelessly communicate with a sensing module of the IMD 16.

The exemplary system 10 may further include additional monitoring apparatus 17 (e.g., a REVEAL cardiac monitor, a FINAPRESS cardiac monitor, nerve activity monitoring apparatus, etc.) to monitor one or more physiological parameters of the patient 14 (e.g., physiological parameters related to the patient's heart 12). For example, the exemplary system 10 may include nerve activity monitoring apparatus that includes needle and/or cuff electrodes configured to monitor vagal activity. The additional monitoring apparatus 17 may be operatively coupled to the IMD 16 and/or any other part of the system 10 to, e.g., share any monitored information to be used in the methods, systems, and devices described herein.

The electrodes 72 may be provided or applied cutaneously or subcutaneously to be located adjacent any of the T1-T12 vertebrae or in any of the C1-C8 locations, and in one or more embodiments, any of the C6-T4 vertebrae, or may be placed adjacent the chest wall. The electrodes 72 may take the form of any of a variety of cutaneous or subcutaneous electrodes. In some embodiments, the electrodes 72 may be disposed immediately adjacent nerve bundles associated with any of the T1-T12 vertebrae.

Conventional subcutaneous electrodes may be surgically inserted into the patient's body. The implantable electrodes may be placed subcutaneously to stimulate underlying muscles, overlying cutaneous nerves, passing somatic nerves, or a combination thereof. For example, various commercially available leads, such as the PISCES, PISCES QUAD PLUS, AND OCTAD model leads, commercially-available from Medtronic Corporation, are examples of leads that may be used for this purpose.

As discussed above, subcutaneous electrodes may be carried on leads and inserted near nerve tissue using a delivery device such as a needle. In other instances, subcutaneous electrodes may be carried on the surface of an implanted medical device such as disclosed in commonly-assigned U.S. Pat. No. 5,292,336 incorporated herein by reference in its entirety. Alternatively, such electrodes may be electrically-isolated from the can, as disclosed in commonly-assigned U.S. Pat. No. 5,331,966 incorporated herein by reference in its entirety.

In one embodiment, a paddle-type (flat) lead having a surface area between about 1 square centimeter and about 30 square centimeters or more may be used to accomplish the subcutaneous stimulation. Such a lead may be formed of an insulative material, with programmable electrodes on one or more of the flat sides of the lead. According to this embodiment, the paddle-type lead may be between four and ten millimeters wide so as to be readily passable through a needle such as a twelve-gage needle before it unfolds. In one embodiment, the delivery needle includes an oval or rectangular cross-section of appropriate size to allow for passage of the lead.

In one or more embodiments described herein, the lead 70, or an equivalent, used in the system 10 may be implanted and temporality coupled to an external medical device (e.g., a SCS stimulator). The exemplary methods described herein for use in determining the effectiveness of a plurality of electrode array configurations may be used while the lead 70 is coupled to the external medical device, e.g., to test the SCS on a patient. Once an electrode configuration is determined effective, and possibly selected, then the lead 70 may be coupled to an implantable medical device such as IMD 16. In other words, the exemplary methods described herein may be used in a temporary, testing period to determine if SCS may be effective to provide cardiac treatment prior to implantation. As such, the IMD 16, or an equivalent, may be used externally (e.g., prior to implantation or long term) to perform any of the methods and/or functionality described herein.

The configuration of the therapy system 10 illustrated in FIG. 1 is merely one example. In other examples, a therapy system may include epicardial leads and/or patch electrodes instead of, or in addition to, the leads 18, 20, 22, 70 illustrated in FIG. 2. Further, in one or more embodiments, the IMD 16 may not be implanted within the patient 14. For example, the IMD 16 may deliver SCS and other therapies via percutaneous leads that extend through the skin of the patient 14 to a variety of positions within the patient's body.

Figure 3:
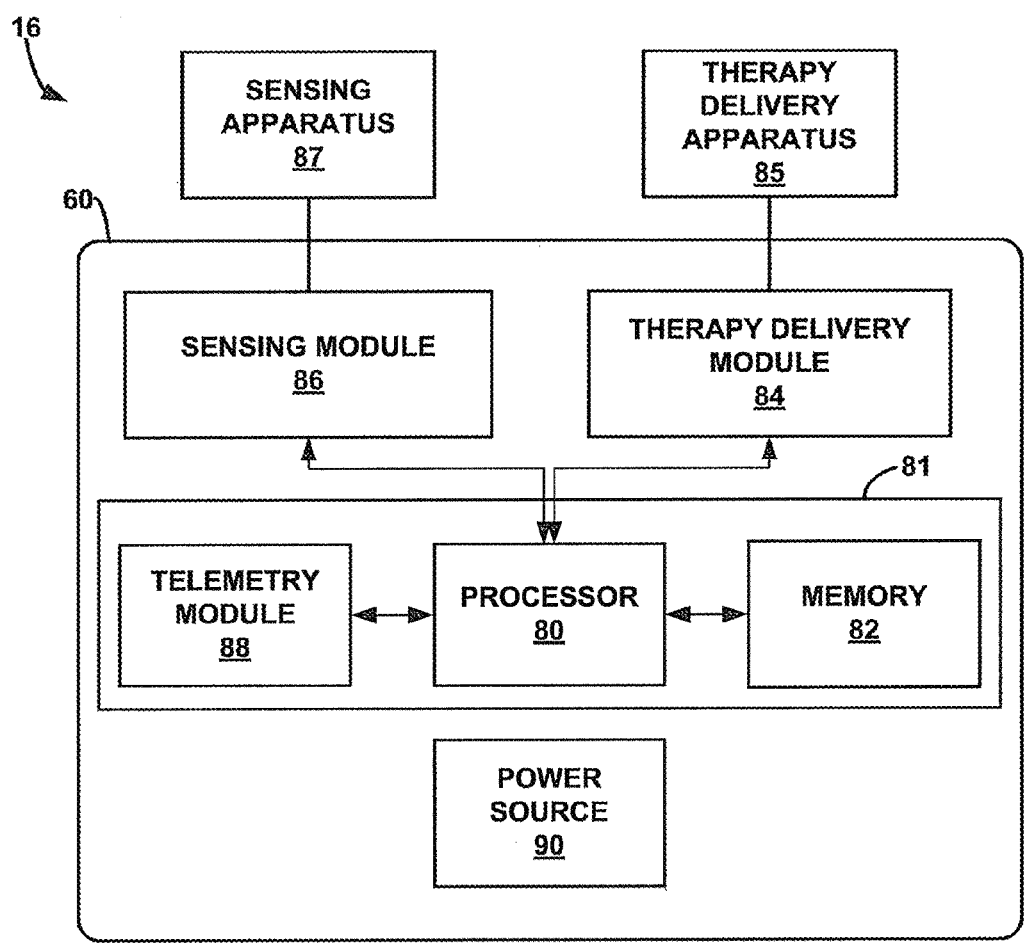
FIG. 3 is a block diagram of the IMD of FIG. 1.

FIG. 3 is a functional block diagram of one exemplary configuration of the IMD 16. As shown, the IMD 16 may include a control module 81, a therapy delivery module 84 (e.g., a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and the control module 81 to perform various functions attributed to the IMD 16 and the control module 81 described herein. Further, the memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The processor 80 of the control module 81 may include any one or more of a microprocessor, a controller, a digital signal processor (DSP), an application specific integrated circuit (ASIC), a field-programmable gate array (FPGA), or equivalent discrete or integrated logic circuitry. In some examples, the processor 80 may include multiple components, such as any combination of one or more microprocessors, one or more controllers, one or more DSPs, one or more ASICs, or one or more FPGAs, as well as other discrete or integrated logic circuitry. The functions attributed to the processor 80 herein may be embodied as software, firmware, hardware, or any combination thereof.

The control module 81 controls the therapy delivery module 84 to deliver therapy (e.g., SCS, electrical stimulation, pacing therapy, etc.) to the spinal cord 13 and/or the heart 12 according to one or more therapy programs, which may be stored in the memory 82. For example, the control module 81 may control the therapy delivery module 84 to deliver electrical pulses with timings, delays, intervals, amplitudes, pulse widths, and/or frequency, via one or more electrode array configurations specified by the one or more therapy programs.

As described herein, the SCS lead 70 may include a plurality of electrodes 72. For example, the SCS lead 70 may include more than or equal to 2 electrodes, 3 electrodes, 4, electrodes, 5 electrodes, 6 electrodes, 8 electrodes, 10 electrodes, etc., and may include less than or equal to 36 electrodes, 32 electrodes, 28 electrodes, 24 electrodes, 20 electrodes, 18 electrodes, 16 electrodes, 14 electrodes, 12 electrodes, 10 electrodes, 8 electrodes, etc.

When the SCS lead 70 is implanted in the patient 14, each electrode 72 may be located in a different location along the patient's spinal cord 13. For example, the electrodes 72 may be spread out or spaced apart longitudinally along the spinal cord 13. Further, each electrode 72 may be selectively configured in an active state (e.g., functional to deliver electrical stimulation) or an inactive state (e.g., nonfunctional to deliver electrical stimulation), and further, may be configured in a negative polarity or in a positive polarity when in an active state.

The control module 81 may control the electrode array configuration of a plurality of SCS electrodes, e.g., the electrodes 72 of the SCS lead 70, to provide a plurality of electrode array configurations. As used herein, an electrode array configuration may be defined as a configuration for the plurality or array of SCS electrodes (e.g., electrodes located on a single lead such as SCS lead 70 or more than one lead) that includes a state (i.e., active or inactive) and a polarity (e.g., positive or negative) for each electrode thereof. Since each electrode may be active or inactive and/or positive or negative when active, a plurality of different electrode array configurations may be possible using the electrodes. Each electrode array configuration of the plurality of electrode array configurations is configured differently than the other electrode array configurations. In other words, each different electrode array configuration will include at least one electrode of the plurality of electrodes that is configured differently (e.g., a different state or polarity) than in every other electrode array configuration.

Figure 4:
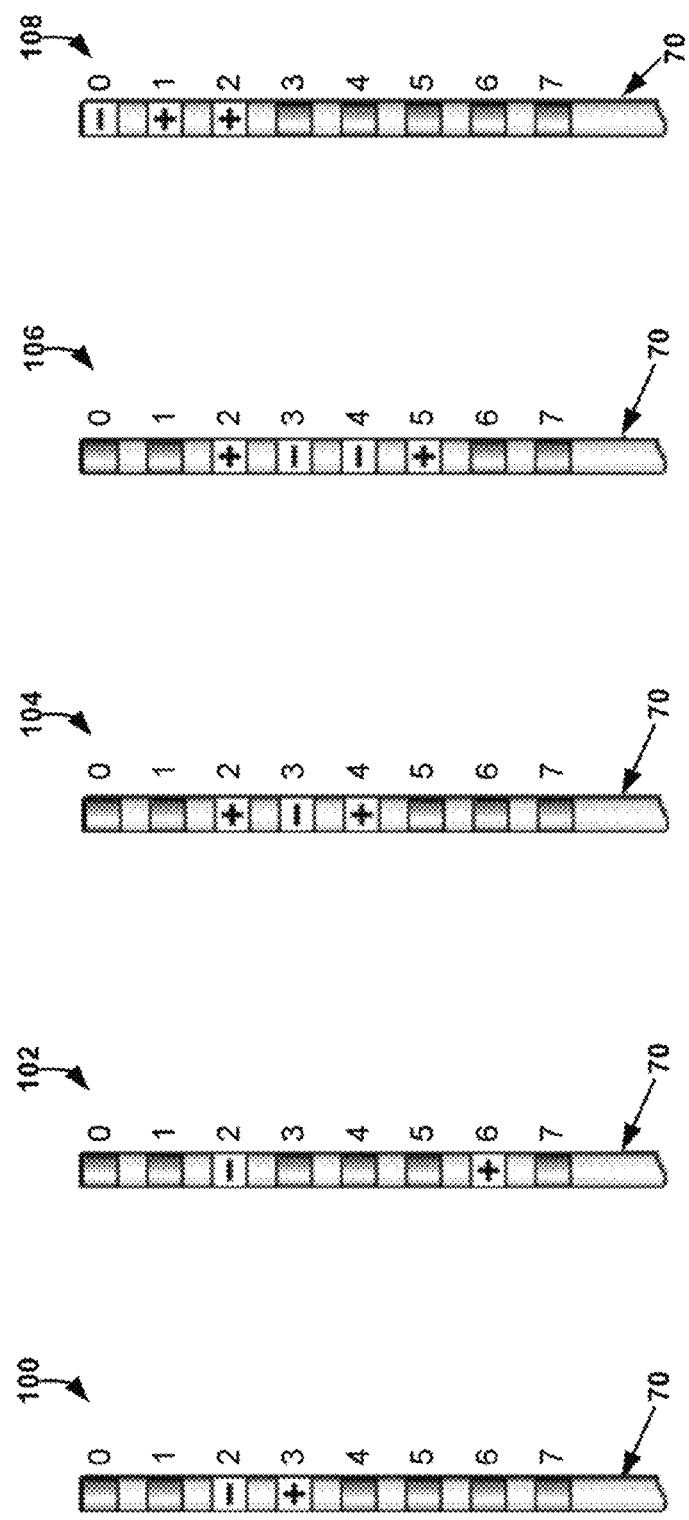
FIG. 4 are exemplary electrode array configurations, e.g., for use with the system of FIG. 1

Exemplary electrode array configurations 100, 102, 104, 106, 108 are depicted in FIG. 4. In the first electrode array configuration 100, electrodes 0-1 and 4-7 are inactive, electrode 2 is active and has a negative polarity, and electrode 3 is active and has a positive polarity. In the second electrode array configuration 102, electrodes 0-1, 3-5, and 7 are inactive, electrode 2 is active and has a negative polarity, and electrode 6 is active and has a positive polarity. In the third electrode array configuration 104, electrodes 0-1 and 5-7 are inactive, electrodes 2 and 4 are active and have a positive polarity, and electrode 3 is active and has a negative polarity. In the fourth electrode array configuration 106, electrodes 0-1 and 6-7 are inactive, electrodes 2 and 5 are active and have a positive polarity, and electrodes 3-4 are active and have a negative polarity. In the fifth electrode array configuration 108, electrodes 3-7 are inactive, electrode 0 is active and has a negative polarity, and electrodes 1-2 are active and have a positive polarity.

A plurality of electrode array configurations may be stored in the memory 82 of the control module 81, and at least one program stored in the memory 82 may control which of the plurality of electrode array configurations may be used to deliver SCS for, or to provide, cardiac therapy (e.g., for use in the treatment of heart failure). Further, at least one therapy program stored in the memory 82 may provide a method to determine or select an effective electrode array configuration from a plurality of different electrode array configurations. For example, as described herein in more detail with respect to one or more exemplary embodiments and FIG. 5, the IMD 16 may perform a method (e.g., stored in the memory 82) to determine or select an effective (e.g., the most effective) electrode array configuration from a plurality of different electrode array configurations to deliver SCS to provide cardiac therapy (e.g., for use in the treatment of heart failure).

The therapy delivery module 84 is coupled (e.g., electrically coupled) to therapy delivery apparatus 85. The therapy deliver apparatus 85 may include, among other therapy delivery devices, the electrodes 40, 42, 44, 46, 48, 50, 58, 62, 64, 66, 72 of the exemplary system of FIG. 1 (e.g., via conductors of the respective leads 18, 20, 22, 70) and/or the housing electrode 58. In one or more embodiments, the therapy delivery module 84 may be configured to generate and deliver electrical stimulation therapy to the spinal cord 13 and/or to the heart 12. For example, therapy delivery module 84 may deliver electrical stimulation via one or more of the electrodes 72.

The sensing module 86 is coupled (e.g., electrically coupled) to sensing apparatus 87, e.g., to monitor signals from the sensing apparatus 87. The sensing apparatus 87 may include the electrodes 40, 42, 44, 46, 48, 50, 58, 62, 64, 66 to monitor electrical activity of the heart 12, e.g., electrocardiogram (ECG) signals, impedance signals between two or more electrodes (e.g., right and/or left ventricle impedance, subcutaneous impedance, impedance waveform during ejection, impedance waveform during filling, etc.), etc. The ECG signals may be used to monitor heart rate (HR), heart rate variability (HRV), heart rate turbulence (HRT), ventricular late potentials, QT dispersion, deceleration/acceleration capacity, deceleration sequence incidence, T-wave alternans (TWA) (which, e.g., is variation in the vector and amplitude of the T-wave component of the EKG), P-wave to P-wave intervals (also referred to as the P-P intervals or A-A intervals), R-wave to R-wave intervals (also referred to as the R-R intervals or V-V intervals), P-wave to QRS complex intervals (also referred to as intrinsic AV conductions, P-R intervals, A-V intervals, or P-Q intervals), QRS-complex morphology, ST segment (i.e., the segment that connects the QRS complex and the T-wave), T-wave changes, QT intervals, electrical vectors, etc. The impedance signals may be used to monitor stroke volume (SV), ejection time (ET), etc.

The sensing apparatus 87 may further include one or more pressure sensors, motion/posture sensors (e.g., 2-D and/or 3-D accelerometers), heart sound sensors, activity sensors, perfusion sensors, etc. to monitor one or more heart-related physiological parameters such as, e.g., activity level, posture, ejection time, stroke volume, cardiac output, pre-ejection time, filling time, normalized ejection time % (ejection time divided by the R-R interval expressed as a percentage), etc.

In some examples, the sensing module 86 may include a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in the memory 82 as an electrocardiogram (ECG). In some examples, the storage of such ECGs in the memory 82 may be under the control of a direct memory access circuit. The processor 80 may employ digital signal analysis techniques to characterize the digitized signals stored in the memory 82 to detect and classify the patient's heart rhythm from the electrical signals. The processor 80 may detect and classify the heart rhythm of the patient by employing any of the numerous signal processing methodologies known in the art.

The telemetry module 88 of the control module 81 may include any suitable hardware, firmware, software, or any combination thereof for communicating with another device, such as the programmer 24 (FIG. 1). For example, under the control of the processor 80, the telemetry module 88 may receive downlink telemetry from and send uplink telemetry to the programmer 24 with the aid of an antenna, which may be internal and/or external to the IMD 16. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer.

In some examples, the control module (e.g., the processor 80) may transmit one or more monitored physiological parameters to the programmer 24, e.g., for evaluation of the effectiveness of an electrode array configuration to be used in the delivery of SCS for, or to provide, cardiac therapy (e.g., for use in the treatment of heart failure). In another example, the control module (e.g., the processor 80) may transmit atrial and ventricular heart signals (e.g., electrocardiogram signals) produced by atrial and ventricular sensing circuits within the sensing module 86 to the programmer 24. The programmer 24 may interrogate the IMD 16 to receive such information (e.g., monitored physiological parameters).

The various components of the IMD 16 may be further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 5:
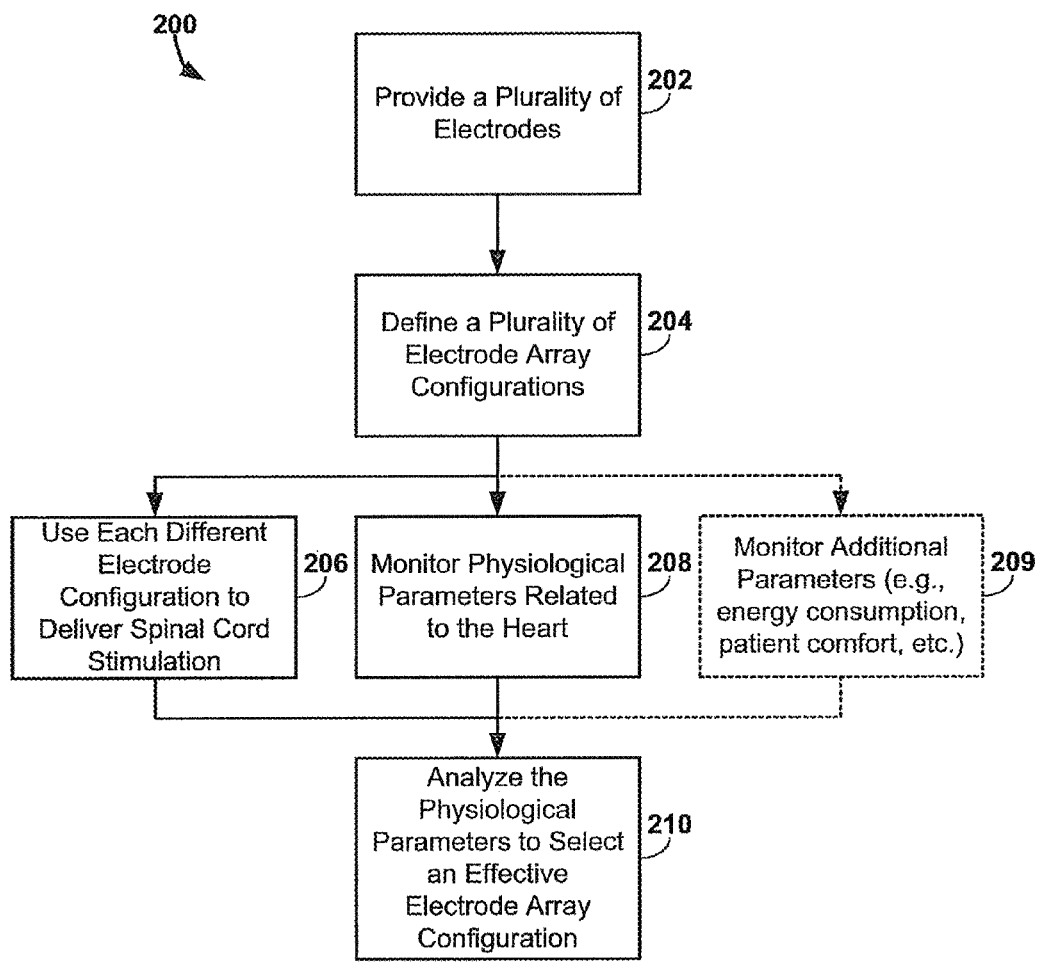
FIG. 5 is a flow chart of an exemplary method for use in delivering spinal cord stimulation for providing cardiac therapy to a patient, e.g., using the system of FIG. 1.

A generalized method 200 for use in a medical device (e.g., the implantable medical device of FIG. 1) operable for delivery of SCS for providing cardiac therapy (e.g., for use in the treatment of heart failure) to a patient is diagrammatically depicted in FIG. 5. Method 200 is intended to illustrate the general functional operation of the devices and/or systems described herein, and should not be construed as reflective of a specific form of software or hardware necessary to practice all of the methods described herein. It is believed that the particular form of software will be determined primarily by the particular system architecture employed in the device (e.g., IMD 16) and by the particular detection and therapy delivery methodologies employed by the device and/or system. Providing software and/or hardware to accomplish the described methods in the context of any modern IMID, given the disclosure herein, is within the abilities of one of skill in the art.

The method 200 of FIG. 5 includes providing a plurality of SCS electrodes 202 located along a patient's spinal cord 13. As described herein the electrodes may be applied cutaneously or subcutaneously adjacent any of the T1-T12 vertebrae or in any of the C1-C8 locations. Each electrode of the plurality of electrodes may be located in a different location along the patient's spinal cord 13. For example, the plurality of electrodes may be spread out or spaced apart along a portion of the patient's spinal cord 13 such that each electrode may affect the patient's spinal cord differently than each of the other electrodes.

A plurality of electrode array configurations using the plurality of electrodes may be defined for use in delivery of spinal cord stimulation 204. As described herein, each electrode array configuration may be different than the other electrode array configurations. In at least one embodiment, the plurality of electrode array configurations may include every different electrode array configuration possible using the plurality of electrodes. In other words, all the different electrode array configurations possible may be defined. Further, in at least another embodiment, the plurality of electrode array configurations may include two electrode array configurations—a first electrode array configuration and a second electrode array configuration that is different than the first electrode array configuration.

Still further, in at least another embodiment, the plurality of electrode array configurations may include any number of electrode array configurations between two electrode array configurations and every different electrode array configuration possible. For example, in a SCS system that may have a possible 36 different electrode array configurations, the plurality of electrode array configurations may include 12 electrode array configurations.

The method 200 further includes using each different electrode array configuration to deliver SCS for, or to provide, cardiac therapy 206 (e.g., for use in the treatment of heart failure) and monitoring one or more physiological parameters related to the patient's heart for each different electrode array configuration of the plurality of defined electrode array configurations 208 (e.g., using the sensing apparatus 87 described herein with reference to FIG. 3, using the additional monitoring apparatus 17 described herein with reference to FIG. 1, etc.). As used herein, physiological parameters that are related to the heart may be any physiological parameter that may provide an indication of the functionality, performance, and/or operation of the heart.

In at least one embodiment, every possible different electrode array configuration using the plurality of electrodes may be used to deliver SCS 206, and the physiological parameters related the patient's heart may be monitored during delivery of SCS from each of the different electrode array configurations. In at least another embodiment, only two different electrode array configurations may be used to deliver SCS 206, and the physiological parameters related the patient's heart may be monitored during delivery of SCS from both of the two different electrode array configurations 208.

Still further, in at least another embodiment, any number of electrode array configurations between two electrode array configurations and every different electrode array configuration possible may be used to deliver SCS 206, and the physiological parameters related the patient's heart may be monitored during delivery of SCS from such any number of electrode array configurations. For example, in a SCS system that may have a possible 36 different electrode array configurations, 12 electrode array configurations may be used to deliver SCS 206, and the physiological parameters related the patient's heart may be monitored during delivery of SCS from each of the 12 electrode array configurations 208.

Various physiological parameters related to the patient's heart may be monitored 208 and may be used to determine whether the SCS applied using an electrode array configuration is effective for cardiac therapy (e.g., for use in the treatment of heart failure). For example, T-wave alternans (TWA), heart rate turbulence (HRT), heart rate variability (HRV), repolarization variability, baroreflex variability, ventricular late potentials, QT dispersion, one or more segments of electrocardiogram (ECG) signals (e.g., Q waves, QRS complexes, etc.), electrical activity of the patient's vagus nerve proximate the patient's heart, etc. may be monitored 208 and may be analyzed to determine whether the SCS applied using an electrode array configuration is effective.

One or more of the physiological parameters monitored 208 may need to be monitored over a selected period time to provide an effective metric to be analyzed for the effectiveness of the SCS being deliver 206. In other words, if a selected time period for the delivery of SCS using an electrode array configuration 206 and the monitoring one or more physiological parameters 208 is too short, the monitored physiological parameters may not be useful to determine the effectiveness of the SCS delivered using the electrode array configuration. As such, SCS using each electrode array configuration may be delivered 206 for a selected period of time that is selected based on the amount of time that may be needed for the monitored one or more physiological parameters to be an effective metric. For example, the selected period of time may be more than or equal to about 1 second, about 2 seconds, about 3 seconds, about 4 seconds, about 5 seconds, about 10 seconds, about 15 seconds, about 20 seconds, about 30 seconds, about 1 minute, about 2 minutes, about 5 minutes, etc., and may be less than or equal to about 5 seconds, 10 seconds, 15 seconds, 20 seconds, 30 seconds, 1 minute, 2 minutes, 5 minutes, 10 minutes, 12 minutes, 15 minutes, 30 minutes, etc.

The selected time period may be dependent on the physiological parameter being monitored to evaluate effective of the electrode array configuration. For example, some physiological parameters may need to be monitored for longer than others. For instance, if the monitor physiological parameters are related to effects on the sympathetic system due to SCS, the selected period of time could be a few seconds. If the monitor physiological parameters SCS are related to an inhibition of sympathetic effect resulting in increase of vagal effect, the selected time period could be about 1 minute or more.

More specifically, if the monitored physiological parameter is heart rate variability in the frequency spectrum, then the selected time period may be about 2 minutes to about 10 minutes. If the monitored physiological parameter is TWA, then the selected time period may be about 30 seconds, or about 20 to about 30 heart beats. Further, HRT depends on premature beats, and thus, a certain number of premature ventricular complexes (e.g., at least 5) may be used to evaluate an electrode array configuration based on HRT.

A partial exemplary listing of select types of sensing mechanisms that may be utilized for monitoring one or more physiological parameters related to a patient's heart for use in determining the effectiveness of an electrode array configuration for, or to provide, cardiac therapy 208 (e.g., for use in the treatment of heart failure) is summarized in Table 1 below. The following table summarizes the types of sensors that may be employed to predict and/or detect a corresponding physiologic condition. Any one or more of the sensing devices and/or other sensing mechanisms known now or developed for sensing physiological parameters may be employed without departing from scope of the present disclosure.

In Table I, column 1 lists general categories of activities, column 2 corresponds to a particular physiologic parameter that may be monitored, column 3 outlines a corresponding sensor or sensing method used to monitor the parameter, and column 4 relates to the type of physiologic condition or occurrence that may be anticipated using the measurement.

TABLE I

Physiological Parameters to be Sensed or Monitored

| GENERAL MODALITY | SPECIFIC ITEMS | SENSING METHODS | WHAT IT CORRESPONDS TO |
| --- | --- | --- | --- |
| Cardiac Electrical Activity | Changes in Morphology of Complexes (QRS, T waves) | ECG, Intracardiac Electrogram (EGM), subcutaneous Electrogram (EGM) | Changes in cardiac depolarization or repolarization patterns |
| | Repolarization Alternans, T Wave Alternans, QRS Alternans, ST Segment Alternans | ECG, Intracardiac EGM subcutaneous EGM | Abnormalities on cardiac electrical depolarization, and repolarization |
| | Heart rate & rhythm (NSVT episodes of VT/VF, PVC's heart rate variability) | ECG, Intracardiac EGM subcutaneous EGM | Cardiac rhythms, regularity |
| | Changes in AV Interval, AV Interval variability, dynamic responses of AV interval to changes in | ECG, Intracardiac EGM subcutaneous EGM | Cardiac conduction abnormalities, autonomic and paracrine modulation of same |

TABLE I-continued

Physiological Parameters to be Sensed or Monitored

| GENERAL MODALITY | SPECIFIC ITEMS | SENSING METHODS | WHAT IT CORRESPONDS TO |
|---|---|---|---|
| | HR<br>Changes in QT Interval<br>QT interval variability,<br>Responses of QT<br>Interval to changes in<br>HR | ECG, Intracardiac<br>EGM subcutaneous<br>EGM | Cardiac repolarization<br>autonomic and paracrine<br>modulations of same |
| Cardiac ischemia | ST Segnment changes, Q<br>Wave, QRS magnitude<br>And width, | ECG, Intracardiac EGM<br>subcutaneous EGM,<br>blood chemistry (sec<br>below) | Mycardial perfusion<br>(balance between supply<br>and demand) |
| Neutral Activity | EEG<br>EGM | Cortical Motor strip<br>Paraspinal muscles<br>Other muscles | Global neutral activity<br>Increases indicate cardiac<br>stress |
| | Certain Nerves | Sympathetic | Increases indicate heart stress |
| | | Parasympathetic | Increases indicate relaxation |
| | | Somatic | Correlates to activity |
| Autonomic Activity | Heart rate variability<br>Baroreflex sensitivity,<br>HR, BP and respiration<br>coupling relationships,<br>Heart rate turbulence | ECG, intracardiac or<br>subcutaneous EGM,<br>Pressure transducer,<br>Lung Impedance | Autonomic tone,<br>baroreflex, respiratory<br>Sinus arrhythmia |
| Hemodynamic Parameters | Arterial or Venous Pressure | Pressure transducer | Systolic Diastolic and Pulse pressure; central venous pressure |
| | Cardiac chamber pressures | Pressure transducer | Developed pressures, peak systolic, diastolic pressures, dP/dt |
| | Cardiac mechanical activity | Accelerometer, sonomicrometer crystals | Tissue displacement, coordination, contraction |
| Blood Chemistry (central arterial and local tissue and differences between these) | $PO_2$, $SAO_2$ | Oximetry, $O_2$ Probe | Related to cardiac performance |
| | Glucose | Oximetry | Indicator of Myocardial Metabolism |
| | Lactate | Oximetry | Indicators of Myocardial Metabolism |
| | $PC\ O_2$ | $C\ O_2$ Probe | Related to cardiac performance |
| | pH | pH Probe | Abnormalities may indicate myocardial electrical instability |
| | Troponin | Molecular Probe | Indicators of Myocardial Ischemia |
| | CKMB | Molecular Probe | Indicators of Myocardial Ischemia |
| | Electrolytes | Molecular Probe | Abnormalities may indicate myocardial electrical instability |
| | Drug levels | Molecular Probe | As indicators of level of protection provided by drug (e.g. antiarrhythmics) |
| | Catecholamines | Molecular Probe | Autonomic Activity/Tone |
| | NO or precursors | Molecular Probe | Related to cardiac injury |
| | Endogneous opiates | Molecular Probe | Autonomic Activity/Tone |

One or more physiological parameters monitored during the delivery of spinal cord stimulation from each different electrode array configuration may be analyzed for effectiveness 210 in providing cardiac therapy (e.g., for use in selection of an effective electrode array configuration of the plurality of electrode array configurations for use in delivering spinal cord stimulation for cardiac therapy (e.g., for use in the treatment of heart failure)). For example, changes (e.g., decrease or increase) in TWA, HRT, HR, repolarization variability, heart rate variability (HRV), the electrical activity of the patient's vagus nerve proximate the patient's heart, and/or baroreflex sensitivity (e.g., the neural component) that correlate to or indicate an improvement in the heart's functionality may indicate that that an electrode array configuration is effective for use in providing cardiac therapy (e.g., for use in the treatment of heart failure). As such, changes (e.g., decrease or increase) in one or more of TWA, HRT, HR, repolarization variability, HRV, the electrical activity of the patient's vagus nerve proximate the patient's heart and/or baroreflex sensitivity (e.g., the neural component) correlate to or indicate an improvement in the heart's functionality may be used to select an electrode array configuration effective for use in providing cardiac therapy.

More specifically, for example, a decrease in TWA may indicate that that an electrode array configuration is effective for use in providing cardiac therapy (e.g., for use in the treatment of heart failure), and as such, a decrease in TWA may be used to select an electrode array configuration effective for use in providing cardiac therapy.

Further, for example, changes in heart rate variability (HRV) may indicate that an electrode array configuration is effective for use in providing cardiac therapy (e.g., for use in the treatment of heart failure). For instance, in the time domain, an increase in the standard deviation in beat-to-beat intervals (SDNN) may indicate that that an electrode array configuration is effective for use in providing cardiac therapy. Further, in the frequency domain, a decrease in low frequency components and an increase in high frequency components may indicate that that an electrode array configuration is effective for use in providing cardiac therapy (e.g., the treatment of heart failure). As such, changes in heart rate variability (HRV), whether in the time domain and/or frequency domain, may be used to select an electrode array configuration effective for use in providing cardiac therapy.

Further, for example, changes in one or more segments of monitored electrocardiogram signals may indicate that an electrode array configuration is effective for use in providing cardiac therapy (e.g., for use in the treatment of heart failure).

After the monitored physiological parameters related to the patient's heart have been analyzed to determine effectiveness of the electrode array configurations for delivering SCS for, or to provide, cardiac therapy (e.g., for use in the treatment of heart failure), one or more electrode array configurations may be selected to deliver SCS for cardiac therapy. In other words, a particular electrode array configuration may be selected to deliver SCS to provide cardiac therapy based on its effectiveness (e.g., the particular electrode array configuration's ability to provide cardiac therapy). In at least one embodiment, the most effective electrode array configuration may be selected to be used to deliver SCS to provide cardiac therapy. For example, the electrode array configuration that provides the lowest monitored TWA may be determined to be the most effective, and therefore, may be selected. Further, for example, the electrode array configuration that provides the greatest monitored baroreflex sensitivity may be determined to be the most effective, and therefore, may be selected.

Selection of an electrode array configuration may not solely be based on the monitored one or more physiological parameters 208 during the delivery of SCS from each electrode array configuration 206. For example, one or more additional parameters (e.g., energy consumption, patient comfort, etc.) may be monitored 209 and may be used to determine or select the electrode array configuration that may be used to deliver SCS for cardiac therapy. In at least one embodiment, the most effective electrode array configuration may not be selected for use in the delivery of SCS to provide cardiac therapy based on such one or more additional monitored parameters.

For instance, an electrode array configuration may be determined to be effective but it may also be determined that is consumes too much power. Another electrode array configuration may be determined to consume less power but be nearly as effective as the former configuration, or effective enough to provide cardiac therapy. In such a situation, the less power-consuming electrode array configuration may be selected although not as effective as the former electrode array configuration (i.e., the electrode array configuration that may consume too much power) because it consumes less power.

Further, for instance, one or more electrode array configurations that are effective may be uncomfortable for a patient, and as such, may not be selected. For example, a patient may provide an indication (e.g., using a button) to the exemplary system that the electrode array configuration presently being used to deliver SCS is uncomfortable.

Further, SCS stimulation using a selected electrode array configuration may become ineffective for various reasons (e.g., after implantation). For example, a spinal lead may shift or move after implantation, and consequently, the electrodes of the spinal lead may have also shifted or moved. As a result, the method 200 may be used to re-select an effective electrode array configuration after the shift or move. In at least one embodiment, this re-selection may occur without the patient seeking a clinician. In other words, the re-selection of the most effective electrode array configuration to deliver SCS for cardiac therapy may be automatic. In at least one embodiment, the effectiveness of the selected SCS electrode array configuration may be evaluated periodically. If it is determined that a more effective SCS electrode array configuration exists to provide cardiac therapy, it may be selected for future SCS for cardiac therapy.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in delivering spinal cord stimulation for providing cardiac therapy comprising:
   stimulation apparatus configured to provide spinal cord stimulation to a patient, wherein the stimulation apparatus comprises a plurality of electrodes located along the patient's spinal cord, wherein each electrode of the plurality of electrodes is locatable at a different location along the patient's spinal cord, wherein each electrode of the plurality of electrodes is configurable in one of an active state and an inactive state and is further configurable in one of a negative polarity and a positive polarity when in the active state;
   sensing apparatus configured to monitor one or more parameters related to the patient's heart; and
   a control module coupled to the sensing apparatus and to the stimulation apparatus and configured to:
      define a plurality of electrode array configurations using the plurality of electrodes for use in delivery of spinal cord stimulation, wherein each electrode array configuration of the plurality of electrode array configurations is configured differently than the other electrode array configurations of the plurality of electrode array configurations,
      use each different electrode array configuration separately from the other electrode array configurations to deliver spinal cord stimulation for cardiac therapy,
      monitor, using the sensing apparatus, one or more physiological parameters related to the patient's heart during the delivery of spinal cord stimulation from each different electrode array configuration of the plurality of electrode array configurations, and analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze T-wave alternans during the delivery of spinal cord stimulation from each different electrode array configuration, determine the effectiveness of each different electrode array configuration based on a decrease in T-wave alternans, and select an effective electrode array configuration from the plurality of electrode array configurations for use in delivering spinal cord stimulation for cardiac therapy based on at least the effectiveness of each different electrode array configuration of the plurality of electrode array configurations, wherein the control module is configured to select an effective electrode array configuration of the plurality of electrode array configurations which, when used to deliver spinal cord stimulation, results in a decrease in T-wave alternans that correlates to an improvement in functionality of the heart of the patient.

2. The system of claim 1, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze heart rate during the delivery of spinal cord stimulation from each different electrode array configuration, and determine the effectiveness of each different electrode array configuration based on a decrease in heart rate.

3. The system of claim 1, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze heart rate variability during the delivery of spinal cord stimulation from each different electrode array configuration, and determine the effectiveness of each different electrode array configuration based on a change in heart rate variability.

4. The system of claim 1, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze repolarization variability during the delivery of spinal cord stimulation from each different electrode array configuration, and determine the effectiveness of each different electrode array configuration based on a decrease in repolarization variability.

5. The system of claim 1, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze baroreflex sensitivity during the delivery of spinal cord stimulation from each different electrode array configuration, and determine the effectiveness of each different electrode array configuration based on an increase in baroreflex sensitivity.

6. The system of claim 1, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze changes in one or more segments of monitored electrocardiogram signals during the delivery of spinal cord stimulation from each different electrode array configuration, and determine the effectiveness of each different electrode array configuration based on the changes in one or more segments of monitored electrocardiogram signals.

7. The system of claim 1, wherein, to analyze the one or more physiological parameters monitored during the delivery of spinal cord stimulation from each different electrode array configuration to select an effective electrode array configuration of the plurality of electrode array configurations for use in delivering spinal cord stimulation for cardiac therapy, the control module is further configured to:

analyze electrical activity of the patient's vagus nerve proximate the patient's heart during the delivery of spinal cord stimulation from each different electrode array configuration, and determine the effectiveness of each different electrode array configuration based on an increase in the electrical activity of the patient's vagus nerve.

8. A system for use in delivering spinal cord stimulation for providing cardiac therapy comprising:

stimulation apparatus configured to provide spinal cord stimulation to a patient, wherein the stimulation apparatus comprises a plurality of electrodes located along a patient's spinal cord, wherein each electrode of the plurality of electrodes is locatable at a different location along the patient's spinal cord, wherein each electrode of the plurality of electrodes is configurable in one of an active state and an inactive state and is further configurable in one of a negative polarity and a positive polarity when in the active state;

sensing apparatus configured to monitor one or more parameters related to the patient's heart; and a control module coupled to the sensing apparatus and to the stimulation apparatus and configured to:

define at least a first electrode array configuration and a second electrode array configuration each for use in delivery of spinal cord stimulation, wherein the first electrode array configuration is configured differently than the second electrode array configuration, use each of the first electrode array configuration and the second electrode array configuration separately from each other to deliver spinal cord stimulation for cardiac therapy, monitor, using the sensing apparatus, one or more physiological parameters related to the patient's heart during the delivery of spinal cord stimulation from each of the first and the second electrode array configurations, and analyze the one or more physiological parameters monitored during the delivery of spinal cord stimulation from each of the first and the second electrode array configurations to determine the more effective electrode array configuration of the first electrode array configuration and the second electrode array configuration for use in delivering spinal cord stimulation for cardiac therapy, wherein, to analyze the one or more physiological parameters monitored during the delivery of spinal cord stimulation from each of the first and second electrode array configurations to select an effective electrode array configuration of the first and second electrode array configurations for use in delivering spinal cord stimulation for cardiac therapy, the control module is further configured to:

analyze T-wave alternans during the delivery of spinal cord stimulation from each of the first and second electrode array configurations, determine the effectiveness of each of the first and second electrode array configurations based on a decrease in T-wave alternans, and select an effective electrode array configuration from the first and second electrode array configurations for use in delivering spinal cord stimulation for cardiac therapy based on at least the effectiveness of each of the first and second electrode array configurations, wherein the control module is configured to select an effective electrode array configuration of the first and second electrode array configurations which, when used to deliver spinal cord stimulation, results in a decrease in T-wave alternans that correlates to an improvement in functionality of the heart of the patient.

9. A method of delivering spinal cord stimulation for providing cardiac therapy comprising:

providing a plurality of electrodes located along a patient's spinal cord, wherein each electrode of the plurality of electrodes is located at a different location along the patient's spinal cord, wherein each electrode of the plurality of electrodes is configurable in one of an active state and an inactive state and is further configurable in one of a negative polarity and a positive polarity when in the active state;

defining a plurality of electrode array configurations using the plurality of electrodes for use in delivery of spinal cord stimulation, wherein each electrode array configuration of the plurality of electrode array configurations is configured differently than the other electrode array configurations of the plurality of electrode array configurations;

using each different electrode array configuration separately from the other electrode array configurations to deliver spinal cord stimulation for cardiac therapy;

monitoring one or more physiological parameters related to the patient's heart during the delivery of spinal cord stimulation from each different electrode array configuration of the plurality of electrode array configurations; and analyzing the one or more physiological parameters monitored during the delivery of spinal cord stimulation from each different electrode array configuration to select an effective electrode array configuration of the plurality of electrode array configurations in delivering spinal cord stimulation for cardiac therapy, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing T-wave alternans during the delivery of spinal cord stimulation from each different electrode array configuration, and determining the effectiveness of each different electrode array configuration based on a decrease in T-wave alternans; and selecting an effective electrode array configuration from the plurality of electrode array configurations for use in delivering spinal cord stimulation for cardiac therapy based on at least the effectiveness of each different electrode array configuration of the plurality of electrode array configurations, wherein the selected effective electrode array configuration of the plurality of electrode array configurations, when used to deliver spinal cord stimulation, results in a decrease in T-wave alternans that correlates to an improvement in functionality of the heart of the patient.

10. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing heart rate turbulence during the delivery of spinal cord stimulation from each different electrode array configuration, and determining the effectiveness of each different electrode array configuration based on a change in heart rate turbulence.

11. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing heart rate during the delivery of spinal cord stimulation from each different electrode array configuration, and determining the effectiveness of each different electrode array configuration based on a decrease in heart rate.

12. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing heart rate variability during the delivery of spinal cord stimulation from each different electrode array configuration, and determining the effectiveness of each different electrode array configuration based on a change in heart rate variability.

13. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing repolarization variability during the delivery of spinal cord stimulation from each different electrode array configuration, and determining the effectiveness of each different electrode array configuration based on a decrease in repolarization variability.

14. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing baroreflex sensitivity during the delivery of spinal cord stimulation from each different electrode array configuration, and determining the effectiveness of each different electrode array configuration based on an increase in baroreflex sensitivity.

15. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing changes in one or more segments of monitored electrocardiogram signals during the delivery of spinal cord stimulation from each different electrode array configuration, and determining the effectiveness of each different electrode array configuration based on the changes in one or more segments of the electrocardiogram signals.

16. The method of claim 9, wherein analyzing the one or more physiological parameters monitored during the delivery of spinal cord stimulation from each different electrode array configuration to select an effective electrode array configuration of the plurality of electrode array configurations for use in delivering spinal cord stimulation for cardiac therapy comprises:

analyzing electrical activity of the patient's vagus nerve proximate the patient's heart during the delivery of spinal cord stimulation from each different electrode array configuration, and determining the effectiveness of each different electrode array configuration based on an increase in the electrical activity of the patient's vagus nerve.

* * * * *